United States Patent
Hughes et al.

(10) Patent No.: US 8,709,191 B2
(45) Date of Patent: *Apr. 29, 2014

(54) LATENT ELASTIC COMPOSITE FORMED FROM A MULTI-LAYERED FILM

(75) Inventors: Janis Wilson Hughes, Alpharetta, GA (US); Glynis Alicia Walton, Roswell, GA (US); Patricia H. Calhoun, Alpharetta, GA (US); Oomman P. Thomas, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1070 days.

This patent is subject to a terminal disclaimer.

(21) Appl. No.: 12/120,984

(22) Filed: May 15, 2008

(65) Prior Publication Data
US 2009/0286444 A1    Nov. 19, 2009

(51) Int. Cl.
*B29C 65/66* (2006.01)
*B29C 55/00* (2006.01)

(52) U.S. Cl.
USPC .......................... 156/229; 264/291

(58) Field of Classification Search
USPC .......................... 156/229; 264/291
See application file for complete search history.

(56) References Cited

U.S. PATENT DOCUMENTS

| | | | |
|---|---|---|---|
| 3,639,917 A | 2/1972 | Althouse | |
| 3,801,429 A | 4/1974 | Schrenk et al. | |
| 3,912,565 A | 10/1975 | Koch et al. | |
| 4,020,141 A | 4/1977 | Quinn et al. | |
| 4,323,534 A | 4/1982 | DesMarais | |
| 4,467,595 A | 8/1984 | Kramers | |
| 4,543,154 A | 9/1985 | Reiter | |

(Continued)

FOREIGN PATENT DOCUMENTS

| EP | 1184914 A1 | 3/2002 |
|---|---|---|
| JP | 2000160463 A | 6/2000 |

(Continued)

OTHER PUBLICATIONS

Product Data Sheet for Exact™ 5361—Plastomer for Polymer Modifications from ExxonMobil Chemical, 1 page, Sep. 2004.

(Continued)

*Primary Examiner* — Scott W Dodds
(74) *Attorney, Agent, or Firm* — Dority & Manning, P.A.

(57) ABSTRACT

A nonwoven composite that exhibits latent elastic properties is provided. The composite is formed from a multi-layered, elastic film laminated to a nonwoven web facing. Latent elasticity is imparted to the composite through the use of at least one base layer that contains a thermoplastic elastomer and at least one skin layer that contains a propylene/α-olefin copolymer. During formation, the film is stretched in one or more directions to orient the elastomer chains. Without intending to be limited by theory, the present inventors believe that the oriented state of the chains may be held in place by the relatively stiff semi-crystalline domains of the propylene/α-olefin copolymer. The stretched elastic film may subsequently be relaxed and bonded to a nonwoven web facing to form the composite. The composite may be later activated (e.g., heated at or above the softening point of the copolymer) to soften the crystalline domains and allow the chains to return to their unoriented state. This causes the film to retract, which forms buckles in the nonwoven facing. In this manner, the resulting composite becomes elastic in that it has the ability to stretch and recover due to the "latent" buckle formation in the nonwoven facing.

21 Claims, 2 Drawing Sheets

(56) References Cited

U.S. PATENT DOCUMENTS

| | | | |
|---|---|---|---|
| 4,552,795 A | 11/1985 | Hansen et al. | |
| 4,640,726 A | 2/1987 | Sallee et al. | |
| 4,640,859 A | 2/1987 | Hansen et al. | |
| 4,663,106 A | 5/1987 | Pomplun et al. | |
| 4,665,306 A | 5/1987 | Roland et al. | |
| 4,680,450 A | 7/1987 | Thorson et al. | |
| 4,720,415 A | 1/1988 | Vander Wielen et al. | |
| 4,789,592 A | 12/1988 | Taniguchi et al. | |
| 4,816,094 A | 3/1989 | Pomplun et al. | |
| 4,834,738 A | 5/1989 | Kielpikowski et al. | |
| 4,916,005 A | 4/1990 | Lippert et al. | |
| 4,940,464 A | 7/1990 | Van Gompel et al. | |
| 4,965,122 A | 10/1990 | Morman | |
| 4,981,747 A | 1/1991 | Morman | |
| 5,003,178 A | 3/1991 | Livesay | |
| 5,093,422 A | 3/1992 | Himes | |
| 5,127,977 A | 7/1992 | Eaton et al. | |
| 5,140,757 A | 8/1992 | Terada | |
| 5,162,074 A | 11/1992 | Hills | |
| 5,169,706 A | 12/1992 | Collier, IV et al. | |
| 5,226,992 A | 7/1993 | Morman | |
| 5,272,236 A | 12/1993 | Lai et al. | |
| 5,278,272 A | 1/1994 | Lai et al. | |
| 5,304,599 A | 4/1994 | Himes | |
| 5,322,728 A | 6/1994 | Davey et al. | |
| 5,332,613 A | 7/1994 | Taylor et al. | |
| 5,336,545 A | 8/1994 | Morman | |
| 5,336,552 A | 8/1994 | Strack et al. | |
| 5,340,431 A | 8/1994 | Terada | |
| 5,368,666 A | 11/1994 | Terada | |
| 5,385,775 A | 1/1995 | Wright | |
| 5,429,856 A | 7/1995 | Krueger et al. | |
| 5,472,775 A | 12/1995 | Obijeski et al. | |
| 5,501,679 A | 3/1996 | Krueger et al. | |
| 5,539,056 A | 7/1996 | Yang et al. | |
| 5,540,796 A | 7/1996 | Fries | |
| 5,571,619 A | 11/1996 | McAlpin et al. | |
| 5,595,618 A | 1/1997 | Fries et al. | |
| 5,620,780 A | 4/1997 | Krueger et al. | |
| 5,691,034 A | 11/1997 | Krueger et al. | |
| 5,773,374 A | 6/1998 | Wood et al. | |
| 5,800,903 A | 9/1998 | Wood et al. | |
| 5,840,412 A | 11/1998 | Wood et al. | |
| 5,885,908 A | 3/1999 | Jaeger et al. | |
| 5,916,203 A | 6/1999 | Brandon et al. | |
| 5,932,497 A | 8/1999 | Morman et al. | |
| 5,997,981 A | 12/1999 | McCormack et al. | |
| 6,015,764 A | 1/2000 | McCormack et al. | |
| 6,060,009 A | 5/2000 | Welygan et al. | |
| 6,090,325 A | 7/2000 | Wheat et al. | |
| 6,111,163 A | 8/2000 | McCormack et al. | |
| 6,197,213 B1 | 3/2001 | Novits et al. | |
| 6,309,736 B1* | 10/2001 | McCormack et al. | 428/198 |
| 6,407,492 B1 | 6/2002 | Avnery et al. | |
| 6,419,798 B1 | 7/2002 | Topolkaraev et al. | |
| 6,436,529 B1 | 8/2002 | Deeb et al. | |
| 6,461,457 B1 | 10/2002 | Taylor et al. | |
| 6,475,600 B1* | 11/2002 | Morman et al. | 428/152 |
| 6,479,154 B1 | 11/2002 | Walton et al. | |
| 6,500,563 B1 | 12/2002 | Datta et al. | |
| 6,559,208 B2 | 5/2003 | Ho et al. | |
| 6,663,611 B2* | 12/2003 | Blaney et al. | 604/385.01 |
| 6,667,351 B2 | 12/2003 | Langohr et al. | |
| 6,709,742 B2 | 3/2004 | Ladika et al. | |
| 6,736,917 B2 | 5/2004 | Tange | |
| 6,794,024 B1 | 9/2004 | Walton et al. | |
| 6,824,734 B2 | 11/2004 | Boggs et al. | |
| 6,861,135 B2 | 3/2005 | Zhou | |
| 6,902,796 B2 | 6/2005 | Morell et al. | |
| 6,916,750 B2 | 7/2005 | Thomas et al. | |
| 6,933,421 B2 | 8/2005 | Topolkaraev et al. | |
| 6,946,413 B2 | 9/2005 | Lange et al. | |
| 6,964,720 B2 | 11/2005 | Schneider et al. | |
| 6,969,441 B2 | 11/2005 | Welch et al. | |
| 6,978,486 B2 | 12/2005 | Zhou | |
| 7,226,880 B2 | 6/2007 | Potnis | |
| 7,270,723 B2 | 9/2007 | McCormack et al. | |
| 7,320,948 B2 | 1/2008 | Morman et al. | |
| 7,582,178 B2* | 9/2009 | Hughes et al. | 156/229 |
| 2002/0009940 A1 | 1/2002 | May et al. | |
| 2004/0110442 A1 | 6/2004 | Rhim | |
| 2005/0101206 A1* | 5/2005 | McCormack et al. | 442/62 |
| 2005/0148263 A1 | 7/2005 | Zhou et al. | |
| 2005/0170729 A1 | 8/2005 | Stadelman et al. | |
| 2005/0245162 A1 | 11/2005 | McCormack et al. | |
| 2006/0003658 A1 | 1/2006 | Hall et al. | |
| 2006/0055089 A1 | 3/2006 | Zhang et al. | |
| 2006/0131783 A1 | 6/2006 | Morman et al. | |
| 2006/0135024 A1 | 6/2006 | Thomas et al. | |
| 2006/0148358 A1 | 7/2006 | Hall et al. | |
| 2006/0151914 A1 | 7/2006 | Gerndt et al. | |
| 2006/0178485 A1* | 8/2006 | Shimakage et al. | 525/242 |
| 2006/0246803 A1 | 11/2006 | Smith et al. | |
| 2006/0251858 A1 | 11/2006 | Thomas et al. | |
| 2007/0045903 A1* | 3/2007 | Day et al. | 264/454 |
| 2007/0137767 A1 | 6/2007 | Thomas et al. | |
| 2007/0141352 A1 | 6/2007 | Calhoun et al. | |
| 2008/0003910 A1* | 1/2008 | Hughes et al. | 442/327 |
| 2008/0119102 A1 | 5/2008 | Hughes et al. | |
| 2008/0119103 A1 | 5/2008 | Ng et al. | |
| 2008/0221540 A1 | 9/2008 | Thomas et al. | |

FOREIGN PATENT DOCUMENTS

| | | |
|---|---|---|
| JP | 2004238775 A | 8/2004 |
| JP | 20070006931 A | 1/2007 |
| JP | WO2007140163 A2 | 12/2007 |
| WO | WO9516425 A2 | 6/1995 |
| WO | WO9516425 A8 | 6/1995 |
| WO | WO9829251 A1 | 7/1998 |
| WO | WO0039201 A2 | 7/2000 |
| WO | WO0039201 A3 | 7/2000 |
| WO | WO0039201 A9 | 7/2000 |
| WO | WO0132116 A1 | 5/2001 |
| WO | WO03031151 A1 | 4/2003 |
| WO | WO03040442 A1 | 5/2003 |
| WO | WO2004020174 A1 | 3/2004 |
| WO | WO2005021262 A1 | 3/2005 |
| WO | WO2005110719 A1 | 11/2005 |
| WO | WO2007070146 A1 | 6/2007 |

OTHER PUBLICATIONS

Product Data Sheet for ExxonMobil PP—PP3155—Homopolymer Grade for Nonwoven and Fiber Applications from ExxonMobil Chemical, 1 page, Aug. 2005.

Product Data Sheet for Vistamaxx™ 1100—Vistamaxx™ Specialty Elastomers from ExxonMobil Chemical, 1 page, 2006.

American Society for Testing Materials (ASTM) Designation: D1238-95 (aka D1238-E), "Standard Test Method for Flow Rates of Thermoplastics by Extrusion Plastometer," pp. 273-281, published Jan. 1996.

American Society for Testing Materials (ASTM) Designation: D2838-02, "Standard Test Method for Shrink Tension and Orientation Release Stress of Plastic Film and Thin Sheeting," pp. 1-4, published Jun. 2002.

American Society for Testing Materials (ASTM) Designation: D5035-95, "Standard Test Method for Breaking Force and Elongation of Textile Fabrics (Strip Method)," pp. 682-688, published Jul. 1995.

Search Report and Written Opinion for PCT/IB2009/051332 dated Feb. 17, 2010, 12 pages.

Supplementary European Search Report dated Aug. 30, 2011, 6 pages.

* cited by examiner

LATENT ELASTIC COMPOSITE FORMED FROM A MULTI-LAYERED FILM

BACKGROUND OF THE INVENTION

Elastic composites are commonly incorporated into products (e.g., diapers, training pants, garments, etc.) to improve their ability to better fit the contours of the body. For example, the elastic composite may be formed from an elastic film and one or more nonwoven web facings. The nonwoven web facing may be joined to the elastic film while the film is in a stretched condition so that the nonwoven web facing can gather between the locations where it is bonded to the film when it is relaxed. The resulting elastic composite is stretchable to the extent that the nonwoven web facing gathered between the bond locations allows the elastic film to elongate. Examples of stretch bonded composites are disclosed, for example, in U.S. Pat. No. 4,720,415 to Vander Wielen et al. Unfortunately, however, the stretchable nature of the composites may cause problems during the manufacturing process of the ultimate products. For example, the force required to unwind the rolled composites may at least partially extend the elastic composite while the elastic article is in tension. This partial extension of the stretchable composite can make it difficult to properly measure and position the desired quantity of the elastic article in the final product.

As such, a need exists for materials that remain relatively inelastic prior to incorporation into a final product, but which achieve a certain level of elasticity after having been activated in the final product.

SUMMARY OF THE INVENTION

In accordance with one embodiment of the present invention, a method of forming a nonwoven composite having latent elasticity is disclosed. The method comprises forming an elastic film that contains a base layer positioned adjacent to a skin layer. The base layer is formed from an elastomeric composition and the skin layer is formed from a thermoplastic composition, wherein about 55 wt. % or more of the polymer content of the elastomeric composition is constituted by at least one substantially amorphous elastomer and about 10 wt. % or more of the polymer content of the thermoplastic composition is constituted by at least one semi-crystalline propylene/α-olefin copolymer. The elastic film is stretched in the machine direction at a stretch ratio from about 1.5 to about 7.0, thereby forming a stretched elastic film. The stretched elastic film is allowed to relax to achieve a relaxation percentage of about 10% or more. A nonwoven web facing is laminated to the relaxed elastic film.

In accordance with another embodiment of the present invention, a nonwoven composite having latent elasticity is disclosed. The composite comprises an elastic film laminated to a nonwoven web facing. The elastic film contains a base layer positioned adjacent to a skin layer. The base layer is formed from an elastomeric composition and the skin layer is formed from a thermoplastic composition, wherein about 55 wt. % or more of the polymer content of the elastomeric composition is constituted by at least one substantially amorphous elastomer and about 10 wt. % or more of the polymer content of the thermoplastic composition is constituted by at least one semi-crystalline propylene/α-olefin copolymer.

In accordance with still another embodiment of the present invention, a method for forming an absorbent article is disclosed. The method comprises fastening a nonwoven composite, such as described above, to one or more components of the article. The nonwoven composite is heated and allowed to retract, thereby increasing the stretchability of the composite.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
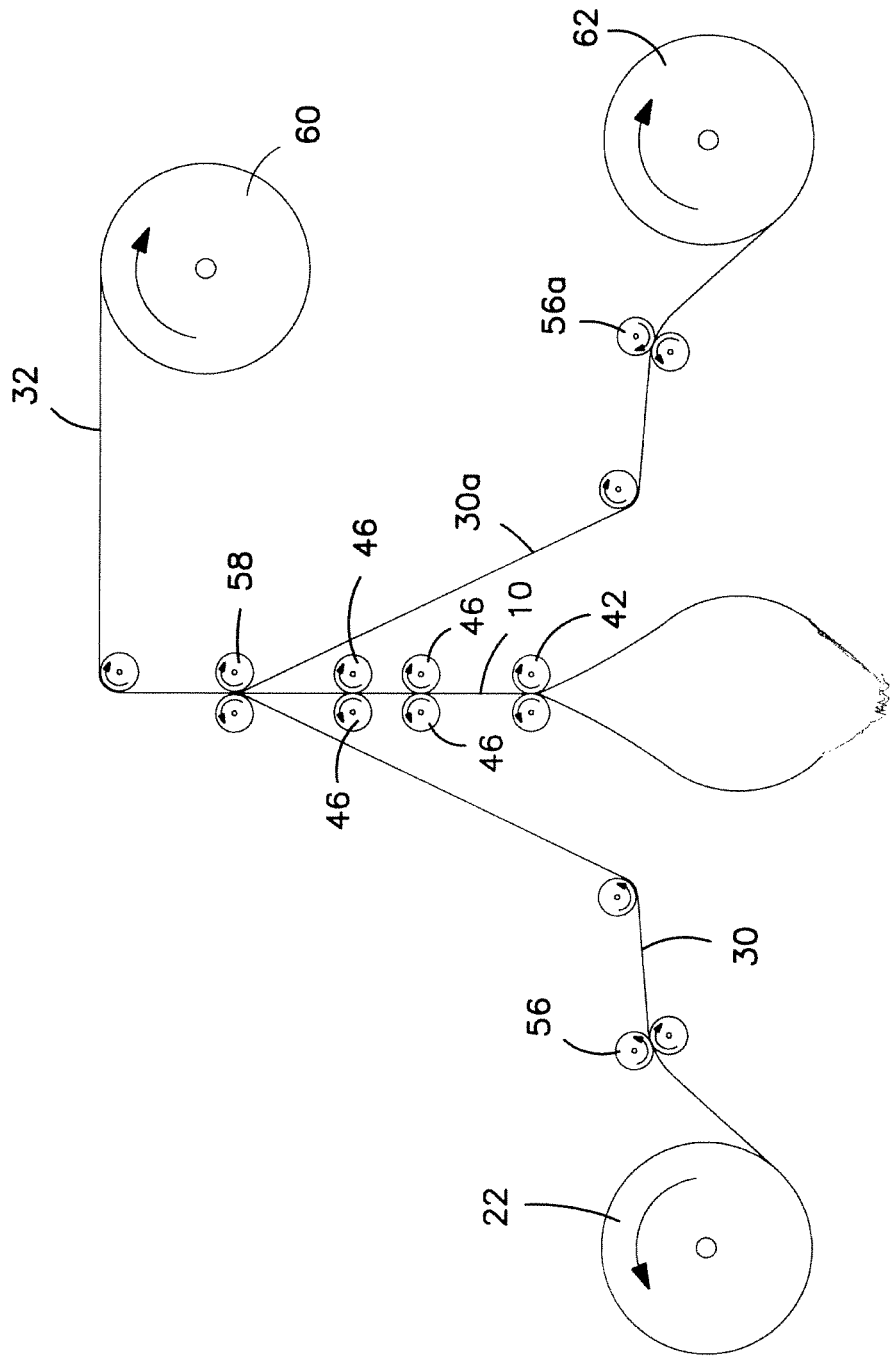
FIG. 1 schematically illustrates a method for forming a composite according to one embodiment of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "nonwoven web" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, carded webs, etc. The basis weight of the nonwoven web may generally vary, such as from about 0.1 grams per square meter ("gsm") to 120 gsm, in some embodiments from about 0.5 gsm to about 70 gsm, and in some embodiments, from about 1 gsm to about 35 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502, 763 to Hartman, U.S. Pat. No. 3,502,538 to Levy, U.S. Pat.

No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

As used herein, the terms "machine direction" or "MD" generally refers to the direction in which a material is produced. The term "cross-machine direction" or "CD" refers to the direction perpendicular to the machine direction. Dimensions measured in the cross-machine direction are referred to as "width" dimension, while dimensions measured in the machine direction are referred to as "length" dimensions.

As used herein, the term "elastomeric" and "elastic" and refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. Desirably, the material contracts or recovers at least 50%, and even more desirably, at least 80% of the stretched length.

As used herein the terms "extensible" or "extensibility" generally refers to a material that stretches or extends in the direction of an applied force by at least about 50% of its relaxed length or width. An extensible material does not necessarily have recovery properties. For example, an elastomeric material is an extensible material having recovery properties. A meltblown web may be extensible, but not have recovery properties, and thus, be an extensible, non-elastic material.

As used herein, the term "set" refers to retained elongation in a material sample following the elongation and recovery, i.e., after the material has been stretched and allowed to relax during a cycle test.

As used herein, the term "percent set" is the measure of the amount of the material stretched from its original length after being cycled (the immediate deformation following the cycle test). The percent set is where the retraction curve of a cycle crosses the elongation axis. The remaining strain after the removal of the applied stress is measured as the percent set.

As used herein, the term "percent stretch" refers to the degree to which a material stretches in a given direction when subjected to a certain force. In particular, percent stretch is determined by measuring the increase in length of the material in the stretched dimension, dividing that value by the original dimension of the material, and then multiplying by 100. Such measurements are determined using the "strip elongation test", which is substantially in accordance with the specifications of ASTM D5035-95. Specifically, the test uses two clamps, each having two jaws with each jaw having a facing in contact with the sample. The clamps hold the material in the same plane, usually vertically, separated by 3 inches and move apart at a specified rate of extension. The sample size is 3 inches by 6 inches, with a jaw facing height of 1 inch and width of 3 inches, and a constant rate of extension of 300 mm/min. The specimen is clamped in, for example, a Sintech 2/S tester with a Renew MTS mongoose box (control) and using TESTWORKS 4.07b software (Sintech Corp, of Cary, N.C.). The test is conducted under ambient conditions. Results are generally reported as an average of three specimens and may be performed with the specimen in the cross direction (CD) and/or the machine direction (MD).

As used herein, the "hysteresis value" of a sample may be determined by first elongating the sample ("load up") and then allowing the sample to retract ("load down"). The hysteresis value is the loss of energy during this cyclic loading.

Detailed Description

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a nonwoven composite that exhibits latent elastic properties. The composite is formed from a multi-layered, elastic film laminated to a nonwoven web facing. Latent elasticity is imparted to the composite through the use of at least one base layer that contains a thermoplastic elastomer and at least one skin layer that contains a propylene/α-olefin copolymer. During formation, the film is stretched in one or more directions to orient the elastomer chains. Without intending to be limited by theory, the present inventors believe that the oriented state of the chains may be held in place by the relatively stiff semi-crystalline domains of the propylene/α-olefin copolymer. The stretched elastic film may subsequently be relaxed and bonded to a nonwoven web facing to form the composite. The composite may be later activated (e.g., heated at or above the softening point of the copolymer) to soften the crystalline domains and allow the chains to return to their unoriented state. This causes the film to retract, which forms buckles in the nonwoven facing. In this manner, the resulting composite becomes elastic in that it has the ability to stretch and recover due to the "latent" buckle formation in the nonwoven facing.

In this regard, various embodiments of the present invention will now be described in greater detail.

I. Multilayered Elastic Film

As indicated above, the film of the present invention contains at least one base layer and at least one skin layer. In one embodiment, for example, the film contains a single base layer positioned adjacent to a single skin layer. In another embodiment, the film contains a single base layer positioned between and adjacent to two skin layers. Regardless of the number employed, the thickness of each individual skin layer is generally selected so as not to substantially impair the elastomeric properties of the film. To this end, a skin layer typically constitutes from about 0.5 wt. % to about 15 wt. % of the film, and in some embodiments, from about 1 wt. % to about 10 wt. % of the film. Likewise, the base layer typically constitutes from about 85 wt. % to about 99.5 wt. % of the film, and in some embodiments, from about 90 wt. % to about 99 wt. % of the film. Each skin layer may also have a thickness (after stretching) of from about 0.1 to about 10 micrometers, in some embodiments from about 0.5 to about 5 micrometers, and in some embodiments, from about 1 to about 2.5 micrometers. Likewise, the base layer may have a thickness (after stretching) of from about from about 1 to about 40 micrometers, in some embodiments from about 2 to about 25 micrometers, and in some embodiments, from about 5 to about 20 micrometers. The film may also have a total thickness (after stretching) of from about 1 to about 100 micrometers, in some embodiments, from about 10 to about 80 micrometers, and in some embodiments, from about 20 to about 60 micrometers.

A. Base Layer

To impart the desired elastic properties to the film, the base layer is formed from an elastomeric composition that is constituted primarily by one or more substantially amorphous elastomers. That is, the elastomers may constitute about 55 wt. % or more, in some embodiments about 60 wt. % or more, and in some embodiments, from about 65 wt. % to 100 wt. % of the polymer content of the elastomeric composition. In fact, in certain embodiments, the base layer may be generally free of polymers that are not substantially amorphous elastomers (e.g., semi-crystalline polyolefins). For example, semi-crystalline polyolefins may constitute about 15 wt. % or less, in some embodiments about 10 wt. % or less, and in some embodiments, about 5 wt. % or less of the polymer content of the elastomeric composition.

Any of a variety of elastomers may generally be employed in the base layer, such as elastomeric polyesters, elastomeric polyurethanes, elastomeric polyamides, elastomeric copolymers, and so forth. For example, the elastomer may be a substantially amorphous block copolymer having at least two blocks of a monoalkenyl arene polymer separated by at least one block of a saturated conjugated diene polymer. The monoalkenyl arene blocks may include styrene and its analogues and homologues, such as o-methyl styrene; p-methyl styrene; p-tert-butyl styrene; 1,3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene blocks may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth. The amount of monoalkenyl arene (e.g., polystyrene) blocks may vary, but typically constitute from about 8 wt. % to about 55 wt. %, in some embodiments from about 10 wt. % to about 35 wt. %, and in some embodiments, from about 25 wt. % to about 35 wt. % of the copolymer. Suitable block copolymers may contain monoalkenyl arene endblocks having a number average molecular weight from about 5,000 to about 35,000 and saturated conjugated diene midblocks having a number average molecular weight from about 20,000 to about 170,000. The total number average molecular weight of the block polymer may be from about 30,000 to about 250,000.

Particularly suitable elastomers are available from Kraton Polymers LLC of Houston, Tex. under the trade name KRATON®. KRATON® polymers include styrene-diene block copolymers, such as styrene-butadiene, styrene-isoprene, styrene-butadiene-styrene, and styrene-isoprene-styrene. KRATON® polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. These block copolymers may have a linear, radial or star-shaped molecular configuration. Specific KRATON® block copolymers include those sold under the brand names G 1652, G 1657, G 1730, MD6673, and MD6937. Various suitable styrenic block copolymers are described in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Other exemplary elastomers that may be used include polyurethane elastomeric materials such as, for example, those available under the trademark ESTANE from Noveon and LYCRA from Invista, polyamide elastomeric materials such as, for example, those available under the trademark PEBAX (polyether amide) from Atofina Chemicals Inc., of Philadelphia, Pa., and polyester elastomeric materials such as, for example, those available under the trade designation HYTREL from E.I. DuPont De Nemours & Company.

Besides elastomers, the base layer may also contain other components as is known in the art. In one embodiment, for example, the base layer contains a filler. Fillers are particulates or other forms of material that may be added to the film polymer extrusion blend and that will not chemically interfere with the film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. Nos. 5,997,981; 6,015,764; and 6,111,163 to McCormack, et al.; U.S. Pat. No. 5,932,497 to Morman, et al.; U.S. Pat. No. 6,461,457 to Taylor, et al., which are incorporated herein in their entirety by reference thereto for all purposes. The fillers may have a spherical or non-spherical shape with average particle sizes in the range of from about 0.1 to about 7 microns. Examples of suitable fillers include, but are not limited to, calcium carbonate, various kinds of clay, silica, alumina, barium carbonate, sodium carbonate, magnesium carbonate, talc, barium sulfate, magnesium sulfate, aluminum sulfate, titanium dioxide, zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as stearic acid, may also be applied to the filler particles if desired. When utilized, the filler content may vary, such as from about 25 wt. % to about 75 wt. %, in some embodiments, from about 30 wt. % to about 70 wt. %, and in some embodiments, from about 40 wt. % to about 60 wt. % of the film.

Other additives may also be incorporated into the film, such as melt stabilizers, processing stabilizers, heat stabilizers, light stabilizers, antioxidants, heat aging stabilizers, whitening agents, antiblocking agents, bonding agents, tackifiers, viscosity modifiers, etc. For example, although the elastomeric polymers may possess a certain amount of tack, a tackifying resin may nevertheless be employed in some embodiments to facilitate subsequent bonding of the film to a nonwoven web facing. One suitable class of tackifying resins includes hydrogenated hydrocarbon resins, such as REGAL-REZ™ hydrocarbon resins available from Eastman Chemical. Other suitable tackifying resins may be described in U.S. Pat. No. 4,787,699. When employed, the tackifying resin may be present in an amount from about 0.001 wt. % to about 35 wt. %, in some embodiments, from about 0.005 wt. % to about 30 wt. %, and in some embodiments, from 0.01 wt. % to about 25 wt. % of the base layer.

Viscosity modifiers may also be employed, such as polyethylene wax (e.g., EPOLENE™ C-10 from Eastman Chemical). Phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant in the production of films. Some suitable hindered phenols include those available from Ciba Specialty Chemicals of under the trade name "Irganox®", such as Irganox® 1076, 1010, or E 201. Moreover, bonding agents may also be added to the film to facilitate bonding of the film to additional materials (e.g., nonwoven web). When employed, additives (e.g., antioxidant, stabilizer, etc.) may each be present in an amount from about 0.001 wt. % to about 40 wt. %, in some embodiments, from about 0.005 wt. % to about 35 wt. %, and in some embodiments, from 0.01 wt. % to about 25 wt. % of the base layer.

B. Skin Layer

The skin layer of the present invention is formed from a thermoplastic composition that contains at least one copolymer of propylene and an α-olefin. Suitable α-olefins may be linear or branched (e.g., one or more $C_1$-$C_3$ alkyl branches, or an aryl group) and formed from olefins, such as $C_2$-$C_{20}$ α-olefins, $C_2$-$C_{12}$ α-olefins, or $C_2$-$C_8$ α-olefins. Specific examples include ethylene, butene; 3-methyl-1-butene; 3,3-dimethyl-1-butene; pentene; pentene with one or more methyl, ethyl or propyl substituents; hexene with one or more methyl, ethyl or propyl substituents; heptene with one or more methyl, ethyl or propyl substituents; octene with one or more methyl, ethyl or propyl substituents; nonene with one or more methyl, ethyl or propyl substituents; ethyl, methyl or dimethyl-substituted decene; dodecene; styrene; and so forth. Particularly desired α-olefin comonomers are ethylene, butene (e.g., 1-butene), hexene, and octene (e.g., 1-octene or 2-octene). Such propylene copolymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich.

Any of a variety of known techniques may generally be employed to form the propylene/α-olefin copolymer. For instance, olefin polymers may be formed using a free radical or a coordination catalyst (e.g., Ziegler-Natta). Preferably, the copolymer is formed from a single-site coordination catalyst, such as a metallocene catalyst. Such a catalyst system produces propylene copolymers in which the comonomer is randomly distributed within a molecular chain and uniformly distributed across the different molecular weight fractions. Metallocene-catalyzed propylene copolymers are described, for instance, in U.S. Pat. No. 7,105,609 to Datta, et al.; U.S. Pat. No. 6,500,563 to Datta, et al.; U.S. Pat. No. 5,539,056 to Yang, et al.; and U.S. Pat. No. 5,596,052 to Resconi, et al., which are incorporated herein in their entirety by reference thereto for all purposes. Examples of metallocene catalysts include bis(n-butylcyclopentadienyl)titanium dichloride, bis (n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

The propylene/α-olefin copolymer is semi-crystalline in nature and may be substantially amorphous in its undeformed state, but form relatively stiff crystalline domains upon stretching. The present inventors have discovered that the relatively stiff crystalline domains present in the skin layer may temporarily hold the chains of the elastomer in place until the film is activated (e.g., heated) to shrink the film and provide the composite with "latent" stretchability. In addition to imparting latent elasticity to the composite, the selection of certain propylene/α-olefin copolymers may result in films with improved strength and elasticity, and may also enhance the ability to form such films. For example, the propylene/α-olefin copolymer employed in the skin layer of the present invention is generally more amorphous than conventional polypropylene homopolymers and thus softer and more elastic in nature. Likewise, the propylene/α-olefin copolymer typically has better melt strength than many other polyolefins (e.g., polyethylenes), thereby allowing the resulting skin layer to provide enhanced structural support to the base layer, which is formed primarily from a soft and low melt strength elastomer.

In this regard, the propylene content of the propylene/α-olefin copolymer is typically from about 60 mole % to about 99.5 mole %, in some embodiments from about 80 mole % to about 99 mole %, and in some embodiments, from about 85 mole % to about 98 mole %. The α-olefin content may likewise range from about 0.5 mole % to about 40 mole %, in some embodiments from about 1 mole % to about 20 mole %, and in some embodiments, from about 2 mole % to about 15 mole %. The distribution of the α-olefin comonomer is typically random and uniform among the differing molecular weight fractions forming the propylene copolymer. The density of the propylene/α-olefin copolymer may be a function of both the length and amount of the α-olefin. That is, the greater the length of the α-olefin and the greater the amount of α-olefin present, the lower the density of the copolymer. Generally speaking, because polymerization with α-olefin comonomers decreases density, the resulting copolymer normally has a density lower than that of certain polyolefins (e.g., LLDPE), but approaching and/or overlapping that of other elastomers. For example, the density of the copolymer may be about 0.91 grams per cubic centimeter ($g/cm^3$) or less, in some embodiments from about 0.85 to about 0.89 $g/cm^3$, and in some embodiments, from about 0.85 $g/cm^3$ to about 0.88 $g/cm^3$.

The degree of crystallinity of the propylene/α-olefin copolymer may also be from about 3% to about 30%, in some embodiments from about 5% to about 25%, and in some embodiments, from about 5% and about 15%. The propylene/α-olefin copolymer may have a latent heat of fusion ($\Delta H_f$), which is another indicator of the degree of crystallinity, of from about 15 to about 75 Joules per gram ("J/g"), in some embodiments from about 20 to about 65 J/g, and in some embodiments, from 25 to about 50 J/g. Further, the propylene/α-olefin copolymer may have a melting temperature ("$T_m$") of from about 100° C. to about 250° C., in some embodiments from about 110° C. to about 200° C., and in some embodiments, from about 140° C. to about 180° C. The propylene/α-olefin copolymer may also have a crystallization temperature ("$T_c$") (determined at a cooling rate of 10° C./min) of from about 50° C. to about 150° C., in some embodiments from about 80° C. to about 140° C., and in some embodiments, from about 100° C. to about 120° C. The latent heat of fusion, melting temperature, and crystallization temperature may be determined using differential scanning calorimetry ("DSC") as is well known to those skilled in the art and described in more detail below.

Propylene/α-olefin copolymers typically constitute about 10 wt. % or more, in some embodiments about 20 wt. % or more, and in some embodiments, from about 30 wt. % to 90 wt. % of the polymer content of the thermoplastic composition used to form the skin layer. Of course, other thermoplastic polymers may also be used so long as they do not adversely affect the desired properties of the composite. For example, the thermoplastic composition may contain other polyolefins (e.g., polypropylene, polyethylene, etc.), polyesters, polyurethanes, polyamides, block copolymers, and so forth. In one embodiment, the thermoplastic composition may contain an additional propylene polymer, such as homopolypropylene or a copolymer of propylene. The additional propylene polymer may, for instance, be formed from a substantially isotactic polypropylene homopolymer or a copolymer containing equal to or less than about 10 wt. % of other monomer, i.e., at least about 90% by weight propylene. Such a polypropylene may be present in the form of a graft, random, or block copolymer and may be predominantly crystalline in that it has a sharp melting point above about 110° C., in some embodiments about above 115° C., and in some embodiments, above about 130° C. Examples of such additional polypropylenes are described in U.S. Pat. No. 6,992,159 to Datta, et al., which is incorporated herein in its entirety by reference thereto for all purposes.

When employed, additional polymer(s) may constitute from about 0.1 wt. % to about 70 wt. %, in some embodiments from about 0.5 wt. % to about 60 wt. %, and in some embodiments, from about 1 wt. % to about 50 wt. % of the thermoplastic composition. Likewise, the above-described propylene/α-olefin copolymer may constitute from about 20 wt. % to about 99.9 wt. %, in some embodiments from about 30 wt. % to about 99.5 wt. %, and in some embodiments, from about 40 wt. % to about 99 wt. % of the thermoplastic composition. Regardless, the melt flow index (MI) of the resulting thermoplastic composition is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 2.16 kilograms in 10 minutes at 190° C., and may be determined in accordance with ASTM Test Method D1238-E.

In addition to polymers, the skin layer may also contain one or more additives (e.g., fillers, antiblocking agents, melt stabilizers, processing stabilizers, heat stabilizers, light stabilizers, antioxidants, heat aging stabilizers, whitening agents, antiblocking agents, bonding agents, tackifiers, viscosity modifiers, etc.), such as described above. When employed, the additives may each be present in an amount from about 0.001 wt. % to about 40 wt. %, in some embodiments, from about 0.005 wt. % to about 35 wt. %, and in some embodiments, from 0.01 wt. % to about 25 wt. % of the skin layer.

The film of the present invention exhibits good latent stretch properties for use in a wide variety of applications. One measurement that is indicative of the latent stretch properties of the film is the heat shrinkage performance, which is a measure of recoverable deformation upon activation. A very high level of heat shrinkage may be achieved in the present invention, such as about 40% or more, in some embodiments about 50% or more, and in some embodiments, about 60% or more. As described in the "Test Methods" below, heat shrinkage is determined by heating the material in water at 160° F. for 30 seconds to 1 minute. Alternatively, shrinkage may be determined using ASTM D2838-02. Any known method of activation may generally be employed in the present invention, including the application of heat, radiation (e.g., microwave), as well as chemical or mechanical treatments. Heat activation may be accomplished at temperatures of from about 50° C. to about 100° C., in some embodiments from about 60° C. to about 90° C., and in some embodiments, from about 70° C. to about 80° C. Any of a variety of techniques may be used to apply heat to the film, such as heated rolls, oven heating, and so forth.

II. Nonwoven Web Facing

A nonwoven web facing is generally employed in the present invention to reduce the coefficient of friction and enhance the cloth-like feel of the composite surface. Exemplary polymers for use in forming nonwoven web facings may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. If desired, biodegradable polymers, such as those described above, may also be employed. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. It should be noted that the polymer(s) may also contain other additives, such as processing aids or treatment compositions to impart desired properties to the fibers, residual amounts of solvents, pigments or colorants, and so forth.

Monocomponent and/or multicomponent fibers may be used to form the nonwoven web facing. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference thereto for all purposes.

Although any combination of polymers may be used, the polymers of the multicomponent fibers are typically made from thermoplastic materials with different glass transition or melting temperatures where a first component (e.g., sheath) melts at a temperature lower than a second component (e.g., core). Softening or melting of the first polymer component of the multicomponent fiber allows the multicomponent fibers to form a tacky skeletal structure, which upon cooling, stabilizes the fibrous structure. For example, the multicomponent fibers may have from about 20% to about 80%, and in some embodiments, from about 40% to about 60% by weight of the low melting polymer. Further, the multicomponent fibers may have from about 80% to about 20%, and in some embodiments, from about 60% to about 40%, by weight of the high melting polymer. Some examples of known sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del.

Fibers of any desired length may be employed, such as staple fibers, continuous fibers, etc. In one particular embodiment, for example, staple fibers may be used that have a fiber length in the range of from about 1 to about 150 millimeters, in some embodiments from about 5 to about 50 millimeters, in some embodiments from about 10 to about 40 millimeters, and in some embodiments, from about 10 to about 25 millimeters. Although not required, carding techniques may be employed to form fibrous layers with staple fibers as is well known in the art. For example, fibers may be formed into a carded web by placing bales of the fibers into a picker that separates the fibers. Next, the fibers are sent through a combing or carding unit that further breaks apart and aligns the fibers in the machine direction so as to form a machine direction-oriented fibrous nonwoven web. The carded web may then be bonded using known techniques to form a bonded carded nonwoven web.

If desired, the nonwoven web facing used to form the nonwoven composite may have a multi-layer structure. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., which are incorporated herein in their entirety by reference thereto for all purposes. In addition, commercially available SMS laminates may be obtained from Kimberly-Clark Corporation under the designations Spunguard® and Evolution®.

Another example of a multi-layered structure is a spunbond web produced on a multiple spin bank machine in which a spin bank deposits fibers over a layer of fibers deposited from a previous spin bank. Such an individual spunbond nonwoven web may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven web may be provided as two or more individually produced layers of a spunbond web, a carded web, etc., which have been bonded together to form the nonwoven web. These individually produced layers may differ in terms of production method, basis weight, composition, and fibers as discussed above.

A nonwoven web facing may also contain an additional fibrous component such that it is considered a composite. For example, a nonwoven web may be entangled with another fibrous component using any of a variety of entanglement techniques known in the art (e.g., hydraulic, air, mechanical, etc.). In one embodiment, the nonwoven web is integrally entangled with cellulosic fibers using hydraulic entanglement. A typical hydraulic entangling process utilizes high pressure jet streams of water to entangle fibers to form a highly entangled consolidated fibrous structure, e.g., a nonwoven web. Hydraulically entangled nonwoven webs of staple length and continuous fibers are disclosed, for example, in U.S. Pat. No. 3,494,821 to Evans and U.S. Pat. No. 4,144,370 to Boulton, which are incorporated herein in their entirety by reference thereto for all purposes. Hydraulically entangled composite nonwoven webs of a continuous fiber nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes. The fibrous component of the composite may contain any desired amount of the resulting substrate. The fibrous component may contain greater than about 50% by weight of the composite, and in some embodiments, from about 60% to about 90% by weight of the composite. Likewise, the nonwoven web may contain less than about 50% by weight of the composite, and in some embodiments, from about 10% to about 40% by weight of the composite.

Although not required, the nonwoven web facing may be necked in one or more directions prior to lamination to the film of the present invention. Suitable necking techniques are described in U.S. Pat. Nos. 5,336,545, 5,226,992, 4,981,747 and 4,965,122 to Morman, as well as U.S. Patent Application Publication No. 2004/0121687 to Morman, et al. Alternatively, the nonwoven web may remain relatively inextensible in at least one direction prior to lamination to the film. In such embodiments, the nonwoven web may be optionally stretched in one or more directions subsequent to lamination to the film.

The basis weight of the nonwoven web facing may generally vary, such as from about 5 grams per square meter ("gsm") to 120 gsm, in some embodiments from about 8 gsm to about 70 gsm, and in some embodiments, from about 10 gsm to about 35 gsm. When using multiple nonwoven web facings, such materials may have the same or different basis weights.

III. Lamination Technique

To achieve the desired latent elasticity of the composite, the multi-layered, elastic film is initially stretched in one or more directions to orient the chains of the elastomer. Thereafter, the stretched material is relaxed to a certain degree and bonded to a nonwoven web facing. Because the film is in a relaxed stated during lamination, the nonwoven web facing does not gather to a significant extent. Thus, despite the fact that the composite contains an elastomer, its elastic properties are initially limited by the presence of the relatively inelastic nonwoven web facing. Upon heat activation, however, the semi-crystalline domains of the propylene/α-olefin copolymer in the skin layer of the film may soften and release the chains from their oriented configuration. This causes the film to further shrink and thereby "gather" the nonwoven web facing. In this manner, the heat-activated composite is provided with latent elasticity.

In this regard, various embodiments of the lamination method will now be described in greater detail. Of course, it should be understood that the description provided below is merely exemplary, and that other methods are contemplated by the present invention. Referring to FIG. 1, for instance, one embodiment of a method for forming a composite from a multi-layered elastic film and a nonwoven web facing is shown. Initially, the raw materials of the base layer (e.g., elastomer) may be added to a first extruder (not shown) and the raw materials of the skin layer (e.g., propylene/α-olefin copolymer, filler, etc.) may be added to a second extruder (not shown). As is well known in the art, the extruders may be connected to a die so that they simultaneously co-extrude a multi-layered film. Alternatively, a single extruder may be employed that is fitted with a multi-manifold die system for producing the layered film.

Any known technique may be used to form a film from the compounded material, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes. For example, in the particular embodiment of FIG. 1, the compounded materials (not shown) are co-extruded together to form a bubble 40 that is supplied between nip rolls 42. Typically, the rolls 42 are kept at temperature sufficient to solidify and quench the elastic film 10 as it is formed, such as from about 20 to 60° C.

As noted above, the latent character of the film of the present invention may be introduced by stretching the film. Although not required, the film may be stretched in-line without having to remove the film for separate processing. For example, the film may be immediately drawn by rolls rotating at different speeds of rotation so that the sheet is stretched to the desired draw ratio in the longitudinal direction (machine direction). In addition, the uniaxially stretched film may also be oriented in the cross-machine direction to form a "biaxially stretched" film. For example, the film may be clamped at its lateral edges by chain clips and conveyed into a tenter oven. In the tenter oven, the film may be drawn in the cross-machine direction to the desired draw ratio by chain clips diverged in their forward travel.

Referring again to FIG. 1, one method for forming a uniaxially stretched film is shown. In the illustrated embodiment, the film is stretched and thinned in the machine direction by passing through a first set of rolls 46 traveling at a speed that is slower than a second set of rolls 46. While four rolls are illustrated in FIG. 1, it should be understood that the number of rolls may be higher or lower, depending on the level of stretch that is desired and the degrees of stretching between each roll. The film may be stretched in either single or multiple discrete stretching operations. Alternatively, the elastic film may also be stretched using a conventional film-orientation unit or machine direction orienter ("MDO"), such as commercially available from Marshall and Williams, Co. of Providence, R.I.

Various parameters of the stretching operation may be selectively controlled, including the draw ratio, stretching temperature, and so forth, to achieve the desired latent elasticity. In some embodiments, for example, the film is stretched in the machine direction at a stretch ratio of from about 1.5 to about 7.0, in some embodiments from about 1.8 to about 5.0, and in some embodiments, from about 2.0 to about 4.5. The stretch ratio may be determined by dividing the length of the stretched film by its length before stretching. The stretch ratio may also be approximately the same as the draw ratio, which may be determined by dividing the linear speed of the film upon stretching (e.g., speed of the nip rolls) by the linear speed at which the film is formed (e.g., speed of casting rolls or blown nip rolls). In the illustrated embodiment, for example, the stretch ratio is determined by dividing the linear speed of the second set of rolls 46 by the linear speed of the nip rolls 42.

The orientation temperature profile is also chosen to deliver the desired shrink mechanical properties, such as shrink tension and shrink percentage. More specifically, the orientation temperature is less than the melting temperature of the propylene/α-olefin copolymer. For example, the film may be stretched at a temperature from about 15° C. to about 50° C., in some embodiments from about 25° C. to about 40° C., and in some embodiments, from about 30° C. to about 40° C. Preferably, the film is "cold drawn", i.e., stretched without the application of external heat (e.g., heated rolls), to improve latent elasticity.

A nonwoven web facing is also employed for laminating to the stretched elastic film 10. For example, a nonwoven web facing 30 may simply be unwound from a supply roll 22 as shown in FIG. 1. Alternatively, the nonwoven web facing may be formed in-line, such as by dispensing polymer filaments from a pair of spinnerettes onto a conveyor assembly. In FIG. 1, the facing 30 is compressed to form inter-filament bonding using a pair of nip rolls 56. Following compaction, the nonwoven web facing 30 is directed to a nip defined between rolls 58 for laminating to the elastic film 10. A second nonwoven web facing 30a may also be employed that originates from a supply roll 62 and passing through nip rolls 56a.

As indicated above, the latent character of the composite of the present invention may be enhanced by allowing the film to relax prior to lamination to a nonwoven web facing. In some embodiments, for example, the elastic film is allowed to relax about 10% or more, in some embodiments from about 15% to about 60%, and in some embodiments, from about 20% to about 50% in the machine direction. The aforementioned "relaxation percentage" may be determined by subtracting the relaxed length of the film by the stretched length of the film, dividing this difference by the stretched length; and then multiplying the quotient by 100. If desired, the stretched and relaxed lengths of the layers may be determined from the speed of rolls used during stretching and lamination. In the illustrated embodiment, for example, the relaxation percentage is determined by subtracting the linear speed of the nip rolls 58 from the linear speed of the rolls 46, dividing this difference by the linear speed of the rolls 46, and then multiplying the quotient by 100.

Various techniques may be utilized to bond the elastic film 10 to the facings 30 and 30a, including adhesive bonding; thermal bonding; ultrasonic bonding; microwave bonding; extrusion coating; and so forth. In one particular embodiment, one or both of the rolls 58 apply a pressure to the film 10 and facings 30 and 30a to thermally bond the materials together. The rolls 58 may be smooth and/or contain a plurality of raised bonding elements. Adhesives may also be employed, such as Rextac 2730 and 2723 available from Huntsman Polymers of Houston, Tex., as well as adhesives available from Bostik Findley, Inc, of Wauwatosa, Wis. The type and basis weight of the adhesive used will be determined on the elastic attributes desired in the final composite and end use. For instance, the basis weight of the adhesive may be from about 1.0 to about 3.0 gsm. The adhesive may be applied to the nonwoven web facings and/or the elastic film prior to lamination using any known technique, such as slot or melt spray adhesive systems.

The resulting composite 32 is wound and stored on a take-up roll 60. Optionally, the composite 32 may be allowed to slightly retract prior to winding on to the take-up roll 60. This may be achieved by using a slower linear velocity for the roll 60. More preferably, however, the composite 32 is kept under tension, such as by using the same linear velocity for the roll 60 as the speed of one or more of the nip rolls 58.

While not shown in FIG. 1, various additional potential processing and/or finishing steps known in the art, such as slitting, treating, printing graphics, etc., may be performed without departing from the spirit and scope of the invention. For instance, the composite may optionally be mechanically stretched in the cross-machine and/or machine directions to enhance extensibility. In one embodiment, the composite may be coursed through two or more rolls that have grooves in the CD and/or MD directions. Such grooved satellite/anvil roll arrangements are described in U.S. Patent Application Publication Nos. 2004/0110442 to Rhim, et al. and 2006/0151914 to Gerndt, et al., which are incorporated herein in their entirety by reference thereto for all purposes. For instance, the laminate may be coursed through two or more rolls that have grooves in the CD and/or MD directions. The grooved rolls may be constructed of steel or other hard material (such as a hard rubber). If desired, heat may be applied by any suitable method known in the art, such as heated air, infrared heaters, heated nipped rolls, or partial wrapping of the laminate around one or more heated rolls or steam canisters, etc. Heat may also be applied to the grooved rolls themselves. It should also be understood that other grooved roll arrangements are equally suitable, such as two grooved rolls positioned immediately adjacent to one another. Besides grooved rolls, other techniques may also be used to mechanically stretch the composite in one or more directions. For example, the composite may be passed through a tenter frame that stretches the composite. Such tenter frames are well known in the art and described, for instance, in U.S. Patent Application Publication No. 2004/0121687 to Morman, et al. The composite may also be necked. Suitable techniques necking techniques are described in U.S. Pat. Nos. 5,336,545, 5,226,992, 4,981,747 and 4,965,122 to Morman, as well as U.S. Patent Application Publication No. 2004/0121687 to Morman, et al., all of which are incorporated herein in their entirety by reference thereto for all purposes.

Generally speaking, composites may be formed according to the present invention that are relatively inelastic prior to heat activation. One parameter that is indicative of the dimensional stability of the composite prior to heat activation is the initial facing-restrained extension percentage of the composite, which is determined according to the test described below and is generally calculated by subtracting the length of the material upon retraction by the length of the material under tension, dividing this value by the length of the material upon retraction, and then multiplying by 100. This is the percent elongation or extension that the composite can undergo before heat activation from a zero tension state to the point at which the facing is fully extended. At this point, the composite is restrained from further elongation without deforming the facing. Typically, the composite of the present invention has an initial facing restrained extension percentage of about 50% or less in the machine direction, in some embodiments about 40% or less in the machine direction, and in some embodiments, about 35% or less in the machine direction prior to heat activation. The potential shrinkage of the composite may also be about 40% or more, in some embodiments about 50% or more, and in some embodiments, about 60% or more.

As a result of the present invention, the composite may be more easily processed into an end product because it is less elastic prior to activation, and thus more dimensionally stable. This allows the composite to be more readily processed, e.g., printed, rolled or unrolled, converted into a final product, etc. In one embodiment, for example, a latent elastic composite may be incorporated into an absorbent article. During the conversion process, the latent elastic composite may be activated through the application of heat, such as during the curing process for an adhesive used to attach together various components of the product. Because the latent elastic composite has a greater dimensional stability prior to activation than highly elastic materials, enhanced processing efficiencies may be realized. For example, the composite need not be maintained in a mechanically stretched condition during attachment to other components of the product. This allows for greater freedom in the location and manner in which the adhesive is applied.

The latent elastic composite of the present invention may be used in a wide variety of applications. As noted above, for example, the composite may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core. In one particular embodiment, the composite of the present invention may be used in providing elastic waist, leg cuff/gasketing, stretchable ear, side panel or stretchable outer cover applications.

Figure 2:
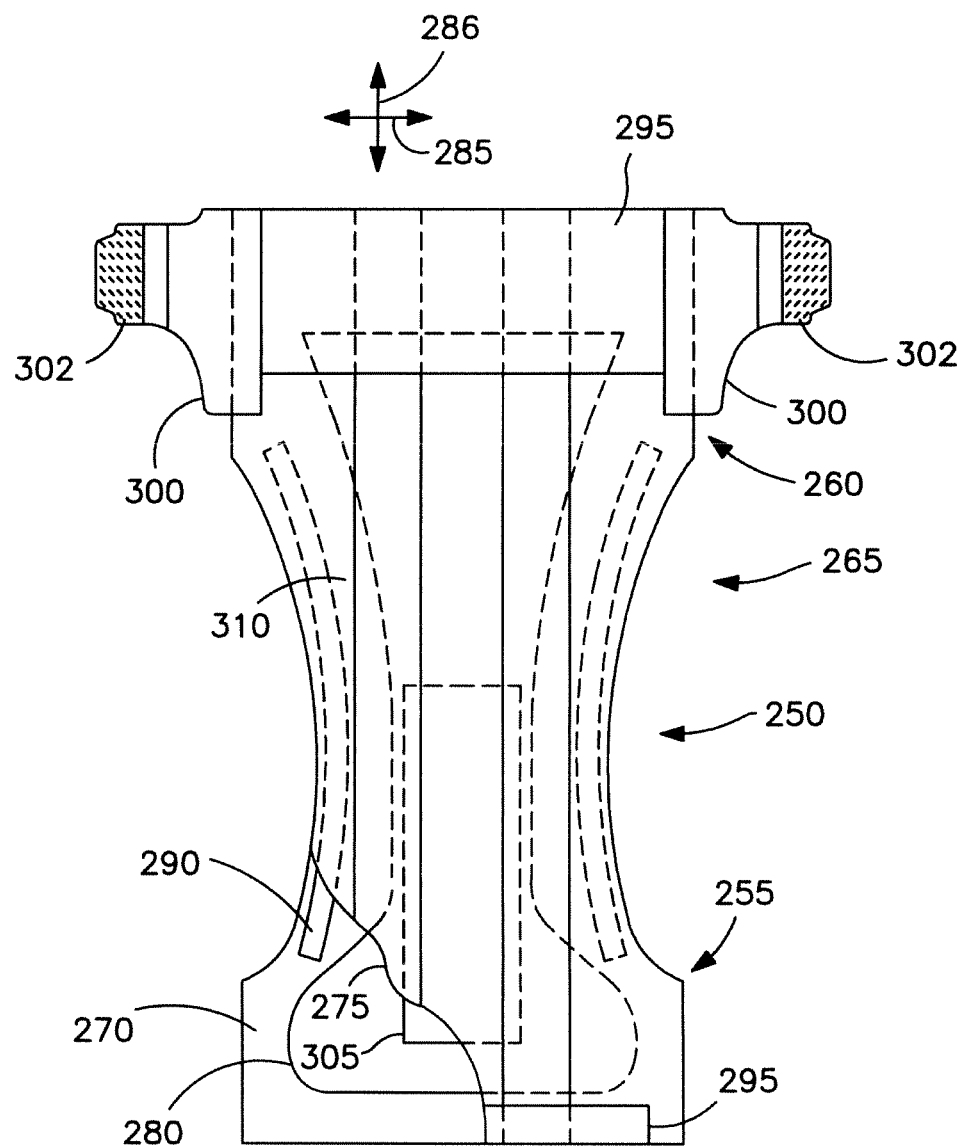
FIG. 2 is a perspective view of a personal care product that may be formed in accordance with one embodiment of the present invention.

Various embodiments of an absorbent article that may be formed according to the present invention will now be described in more detail. Referring to FIG. 2, for example, one embodiment of a disposable diaper 250 is shown that generally defines a front waist section 255, a rear waist section 260, and an intermediate section 265 that interconnects the front and rear waist sections. The front and rear waist sections 255 and 260 include the general portions of the diaper which are constructed to extend substantially over the wearer's front and rear abdominal regions, respectively, during use. The intermediate section 265 of the diaper includes the general portion of the diaper that is constructed to extend through the wearer's crotch region between the legs. Thus, the intermediate section 265 is an area where repeated liquid surges typically occur in the diaper.

The diaper 250 includes, without limitation, an outer cover, or backsheet 270, a liquid permeable bodyside liner, or topsheet, 275 positioned in facing relation with the backsheet 270, and an absorbent core body, or liquid retention structure, 280, such as an absorbent pad, which is located between the backsheet 270 and the topsheet 275. The backsheet 270 defines a length, or longitudinal direction 286, and a width, or lateral direction 285 which, in the illustrated embodiment, coincide with the length and width of the diaper 250. The liquid retention structure 280 generally has a length and width that are less than the length and width of the backsheet 270, respectively. Thus, marginal portions of the diaper 250, such as marginal sections of the backsheet 270 may extend past the terminal edges of the liquid retention structure 280. In the illustrated embodiments, for example, the backsheet 270 extends outwardly beyond the terminal marginal edges of the liquid retention structure 280 to form side margins and end margins of the diaper 250. The topsheet 275 is generally coextensive with the backsheet 270 but may optionally cover an area that is larger or smaller than the area of the backsheet 270, as desired.

To provide improved fit and to help reduce leakage of body exudates from the diaper 250, the diaper side margins and end margins may be elasticized with suitable elastic members, as further explained below. For example, as representatively illustrated in FIG. 2, the diaper 250 may include leg elastics 290 constructed to operably tension the side margins of the diaper 250 to provide elasticized leg bands which can closely fit around the legs of the wearer to reduce leakage and provide improved comfort and appearance. Waist elastics 295 are employed to elasticize the end margins of the diaper 250 to provide elasticized waistbands. The waist elastics 295 are configured to provide a resilient, comfortably close fit around the waist of the wearer. The latently elastic materials of the present invention are suitable for use as the leg elastics 290 and waist elastics 295. Exemplary of such materials are laminate sheets that either comprise or are adhered to the backsheet, such that elastic constrictive forces are imparted to the backsheet 270.

As is known, fastening means, such as hook and loop fasteners, may be employed to secure the diaper 250 on a wearer. Alternatively, other fastening means, such as buttons, pins, snaps, adhesive tape fasteners, cohesives, fabric-and-loop fasteners, or the like, may be employed. In the illustrated embodiment, the diaper 250 includes a pair of side panels 300 (or ears) to which the fasteners 302, indicated as the hook portion of a hook and loop fastener, are attached. Generally, the side panels 300 are attached to the side edges of the diaper in one of the waist sections 255, 260 and extend laterally outward therefrom. The side panels 300 may be elasticized or otherwise rendered elastomeric by use of a latently elastic materials of the present invention. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

The diaper 250 may also include a surge management layer 305, located between the topsheet 275 and the liquid retention structure 280, to rapidly accept fluid exudates and distribute the fluid exudates to the liquid retention structure 280 within the diaper 250. The diaper 250 may further include a ventilation layer (not illustrated), also called a spacer, or spacer layer, located between the liquid retention structure 280 and the backsheet 270 to insulate the backsheet 270 from the liquid retention structure 280 to reduce the dampness of the garment at the exterior surface of a breathable outer cover, or backsheet, 270. Examples of suitable surge management layers 305 are described in U.S. Pat. No. 5,486,166 to Bishop and U.S. Pat. No. 5,490,846 to Ellis.

As representatively illustrated in FIG. 2, the disposable diaper 250 may also include a pair of containment flaps 310 which are configured to provide a barrier to the lateral flow of body exudates. The containment flaps 310 may be located along the laterally opposed side edges of the diaper adjacent the side edges of the liquid retention structure 280. Each containment flap 310 typically defines an unattached edge that is configured to maintain an upright, perpendicular configuration in at least the intermediate section 265 of the diaper 250 to form a seal against the wearer's body. The containment flaps 310 may extend longitudinally along the entire length of the liquid retention structure 280 or may only extend partially along the length of the liquid retention structure. When the containment flaps 310 are shorter in length than the liquid retention structure 280, the containment flaps 310 can be selectively positioned anywhere along the side edges of the diaper 250 in the intermediate section 265. Such containment flaps 310 are generally well known to those skilled in the art. For example, suitable constructions and arrangements for containment flaps 310 are described in U.S. Pat. No. 4,704,116 to Enloe.

The diaper 250 may be of various suitable shapes. For example, the diaper may have an overall rectangular shape, T-shape or an approximately hour-glass shape. In the shown embodiment, the diaper 250 has a generally I-shape. Other suitable components which may be incorporated on absorbent articles of the present invention may include waist flaps and the like which are generally known to those skilled in the art. Examples of diaper configurations suitable for use in connection with the latently elastic materials of the present invention that may include other components suitable for use on diapers are described in U.S. Pat. No. 4,798,603 to Meyer et al.; U.S. Pat. No. 5,176,668 to Bernardin; U.S. Pat. No. 5,176,672 to Bruemmer et al.; U.S. Pat. No. 5,192,606 to Proxmire et al.; and U.S. Pat. No. 5,509,915 to Hanson et al., which are incorporated herein in their entirety by reference thereto for all purposes.

The various regions and/or components of the diaper 201 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the topsheet 275 and backsheet 270 may be assembled to each other and to the liquid retention structure 280 with lines of adhesive, such as a hot melt, pressure-sensitive adhesive. Similarly, other diaper components, such as the elastic members 290 and 295, fastening members 302, and surge layer 305 may be assembled into the article by employing the above-identified attachment mechanisms.

Although various configurations of a diaper have been described above, it should be understood that other diaper and absorbent article configurations are also included within the scope of the present invention. In addition, the present invention is by no means limited to diapers. In fact, several examples of absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Further, other examples of personal care products that may incorporate such materials are training pants (such as in side panel materials) and feminine care products. By way of illustration only, training pants suitable for use with the present invention and various materials and methods for constructing the training pants are disclosed in U.S. Pat. No. 6,761,711 to Fletcher et al.; U.S. Pat. No. 4,940,464 to Van Gompel et al.; U.S. Pat. No. 5,766,389 to Brandon et al.; and U.S. Pat. No. 6,645,190 to Olson et al., which are incorporated herein in their entirety by reference thereto for all purposes.

The present invention may be better understood with reference to the following examples.

Test Methods

% Heat Shrinkage

To measure heat-activated retraction, two marks are placed 100 millimeters apart on the material (while still under tension on a roll) to define a sample length of 100 millimeters. The material is then released from tension on the roll and a length of material containing the marks is cut from the roll. Immediately after releasing the material and cutting it, the distance between the marks is measured again to determine the initial length (Before Heated Retraction Length or "BHRL"). The initial facing restrained extension percentage (before heat activation) of the composite is calculated by the following equation:

% extension=100*(100−BHRL)/BHRL

The material is then submerged in water (160° F.) for at least 30 seconds, but no more than 1 minute. Thereafter, the distance between the marks is again measured (After Heated Retraction Length or "AHRL"). The percent shrinkage is indicative of the latent elasticity of the material and is calculated by the following equation:

% shrinkage=100*(BHRL−AHRL)/BHRL

Three measurements are averaged for each sample to be tested. The measurements are taken at ambient conditions.

Cycle Testing

The materials were tested using a cyclical testing procedure to determine load loss and percent set. In particular, 2-cycle testing was utilized to 100% defined elongation. For this test, the sample size was 3 inches (7.6 centimeters) in the cross-machine direction by 6 inches in the machine direction. The Grip size was 3 inches (7.6 centimeters) in width. The grip separation was 4 inches. The samples were loaded such that the machine direction of the sample was in the vertical direction. A preload of approximately 20 to 30 grams was set. The test pulled the sample to 100% elongation at a speed of 20 inches (50.8 centimeters) per minute, and then immediately (without pause) returned to the zero at a speed of 20 inches (50.8 centimeters) per minute. The results of the test data are all from the first and second cycles. The testing was done on a Sintech Corp. constant rate of extension tester 2/S with a Renew MTS mongoose box (control) using TESTWORKS 4.07b software (Sintech Corp, of Cary, N.C.). The tests were conducted under ambient conditions.

Load Loss

The percent load loss was determined using a stress relaxation experiment with a one-inch wide by seven (7) inch long sample strip. The ends of the strip are clamped into a Sintech 1/S or 2/S frame equipped with TESTWORKS software to record data. Two (2) inches of the strip length were maintained within the clamping jaws on both ends, and three (3) inches of the length were exposed. The testing apparatus was maintained in a 100° F. controlled temperature chamber. The strip was stretched at a rate of 40 inches per minute to an elongation of 50%, and was maintained in the stretched condition for twelve (12) hours. The load was measured and plotted as a function of time, typically yielding a curve which showed exponential load loss. The percent load loss over time (t) was determined from the following equation:

% Load Loss=Load(t=0 hours)−Load(t=12 hours)×100/Load(t=0 hours)

wherein, t=time, in hours.

EXAMPLE 1

A film was formed having a multi-layered "skin-core" structure. The core comprised 94 wt. % of the film and the skin layer comprised 6 wt. % of the film. The core was formed from 75% percent of KRATON® MD6673 (Kraton Polymers, LLC of Houston Tex.) and 25% of EXACT™ 5361 (ExxonMobil Chemical Co.). The skin layer was formed from 50% VISTAMAXX™ 1100 (ExxonMobil Chemical Co.) and a filler compound (Standridge Color Corp.), which contained calcium carbonate blended with polypropylene and polypropylene random copolymers. KRATON® MD6673 contains 68 wt. % of a styrene-ethylene-butylene-styrene ("SEBS") block copolymer (KRATON® MD6937), 20 wt. % REGALREZ™ 1126 (Eastman Chemical), and 12 wt. % EPOLENE™ C-10 polyethylene wax (Eastman Chemical). VISTAMAXX™ 1100 is a metallocene-catalyzed propylene/ethylene copolymer having a density of 0.862 g/cm$^3$.

The polymers were compounded by weighing appropriate portions of pellets of each polymer, combining them into one container, and mixing them together by stirring. After compounding, the sample was extruded using a small scale triple screw blown film line with a 1.75-inch extruder (Killion) and two 16-millimeter extruders (Collin GmbH). The blown film line also employed an air ring (Collin GmbH), 3-inch die (Collin GmbH), and collapsing tower (Killion). Each extruder had three temperature zones and a die with a controlled temperature. The core layer was extruded from the 1.75-inch, and the skin layer was extruded from one of the second 16-mm extruders. The temperature profile for the core extruder was arranged so that a melt temperature of about 375° F. was achieved. The temperature profile for the skin extruder was arranged so that a melt temperature of about 190° F. was achieved.

After quenching from the air ring and collapsing the bubble (collapsing nip was run at 23 feet per minute), the film was stretched in the machine direction between two sets of driven nips. The first nip ran at 23 feet per minute and the second nip ran at 68 feet per minute (stretch ratio of about 3.0). The film was then relaxed 30% and fed through a rotary bonder running at 47 feet per minute. The rotary bonder had a square diamond bond pattern with a bond area of 8%-14% and a pin density of 52 pins per square inch. Anvil and patterned rolls were employed at 150° F. and a pressure of 117 pounds per linear inch. The film was bonded to a polypropylene spunbond facing having a basis weight of approximately 13.6 grams per square meter. The resulting laminate was wound so as to maintain the stretch at the winder.

EXAMPLE 2

A film was formed having a multi-layered "skin-core" structure. The core comprised 90 wt. % of the film and the skin layer comprised 10 wt. % of the film. The core was formed from 100% percent of KRATON® MD6673 (Kraton Polymers, LLC of Houston Tex.). The skin layer was formed from 50% VISTAMAXX™ 1100 (ExxonMobil Chemical Co.) and a filler compound (Standridge Color Corp.), which contained calcium carbonate blended with polypropylene and polypropylene random copolymers.

The polymers were compounded by weighing appropriate portions of pellets of each polymer, combining them into one container, and mixing them together by stirring. After compounding, the sample was extruded using a small scale triple screw blown film line with a 1.75-inch extruder (Killion) and two 16-millimeter extruders (Collin GmbH). The blown film line also employed an air ring (Collin GmbH), 3-inch die (Collin GmbH), and collapsing tower (Killion). Each extruder had three temperature zones and a die with a controlled temperature. The core layer was extruded from the 1.75-inch, and the skin layer was extruded from one of the second 16-mm extruders. The temperature profile for the core extruder was arranged so that a melt temperature of about 375° F. was achieved. The temperature profile for the skin extruder was arranged so that a melt temperature of about 190° F. was achieved.

After quenching from the air ring and collapsing the bubble (collapsing nip was run at 22 feet per minute), the film was stretched in the machine direction between two sets of driven nips. The first nip ran at 22 feet per minute and the second nip ran at 67 feet per minute (stretch ratio of about 3.0). The film was then relaxed 30% and fed through a rotary bonder running at 47 feet per minute. The rotary bonder had a square diamond bond pattern with a bond area of 8%-14% and a pin density of 52 pins per square inch. Anvil and patterned rolls were employed at 150° F. and a pressure of 117 pounds per linear inch. The film was bonded to a polypropylene spunbond facing having a basis weight of approximately 13.6 grams per square meter. The resulting laminate was wound so as to maintain the stretch at the winder. The materials of Examples 1 and 2 were then heat activated in hot water at 160° F. for 30 seconds, and also "cycle" tested and "stress relaxation" tested. The results are set forth below in Tables 1-3.

results for Sample 2 showed superior performance as exhibited by a lower % load loss. Both samples exhibited good latency behavior through their BHRL and AHRL results.

EXAMPLE 3

Formation was attempted of a film having a multi-layered "skin-core" structure. The core comprised 90 wt. % of the film and the skin layer comprised 10 wt. % of the film. The core was formed from 100% percent of KRATON® MD6673 (Kraton Polymers, LLC of Houston Tex.). The skin layer was formed from 10% 640I (Dow Plastics) and 90% of EXACT™ 5361 (ExxonMobil Chemical Co.). "640I" is a low density polyethylene ("LDPE") having a density of 0.92 g/cm³ and "EXACT™ 5361" is a metallocene-catalyzed ethylene/octene copolymer having a density of 0.86 g/cm³. The polymers were compounded by weighing appropriate portions of pellets of each polymer, combining them into one container, and mixing them together by stirring. After compounding, the sample was extruded using a small scale triple screw blown film line with a 1.75-inch extruder (Killion) and two 16-millimeter extruders (Collin GmbH). The blown film line also employed an air ring (Collin GmbH), 3-inch die (Collin GmbH), and collapsing tower (Killion). Each extruder had three temperature zones and a die with a controlled temperature. The core layer was extruded from the 1.75-inch, and the skin layer was extruded from one of the second 16-mm extruders. The temperature profile for the core extruder was arranged so that a melt temperature of about 375° F. was

TABLE 1

| | Process Conditions | | | | | | | |
|---|---|---|---|---|---|---|---|---|
| Sample | Core Extruder Speed (RPM) | Skin Extruder Speed (RPM) | Nip #1 Speed (ft/min) | Stretch Ratio | Nip #2 Speed (ft/min) | Relaxation % | Bonder Speed (ft/min) | Winder Speed (ft/min) |
| 1 | 37 | 27 | 23 | 3 | 68 | 30 | 47 | 47 |
| 2 | 35 | 35 | 22 | 3 | 67 | 30 | 47 | 47 |

TABLE 2

| | | | | | Shrinkage and Cycle Results | | | | | | | |
|---|---|---|---|---|---|---|---|---|---|---|---|---|
| | | | | | | Cycle 1 | | | | Cycle 2 | | |
| Sample | BHRL (mm) | AHRL (mm) | % Initial Composite Extension | % Shrinkage | Load up 50% | Load up 100% | Load down 50% | Hyst. % | Load up 50% | Load up 100% | Load down 50% | Set % |
| 1 | 84 | 53 | 19 | 37 | 1334 | 2078 | 818 | 34.2 | 1083 | 2014 | 818 | 13.4 |
| 2 | 78 | 55 | 28 | 30 | 1226 | 1716 | 821 | 29.9 | 1040 | 1676 | 809 | 9.9 |

TABLE 3

| Stress Relaxation Results | |
|---|---|
| Sample | % Load Loss |
| 1 | 40.7 |
| 2 | 36.8 |

As indicated, Sample 2 provided improved elastic behavior compared to Sample 1 after heat activation as exhibited by lower hysteresis and percent set. Further, the stress relaxation achieved. The temperature profile for the skin extruder was arranged so that a melt temperature of about 190° F. was achieved.

The skin layer did not stabilize the core layer and the film was unstable after the die exit. This formulation was unable to successfully form a film.

While the invention has been described in detail with respect to the specific embodiments thereof, it will be appreciated that those skilled in the art, upon attaining an understanding of the foregoing, may readily conceive of alterations to, variations of, and equivalents to these embodiments.

Accordingly, the scope of the present invention should be assessed as that of the appended claims and any equivalents thereto.

What is claimed is:

1. A method of forming a nonwoven composite having latent elasticity, the method comprising:

forming an elastic film that contains a base layer positioned adjacent to a skin layer, wherein the base layer is formed from an elastomeric composition and the skin layer is formed from a thermoplastic composition, wherein about 55 wt. % or more of the polymer content of the elastomeric composition is constituted by at least one substantially amorphous elastomer and about 10 wt. % or more of the polymer content of the thermoplastic composition is constituted by at least one semi-crystalline propylene/α-olefin copolymer;

stretching the elastic film in the machine direction at a stretch ratio from about 1.5 to about 7.0 without applying external heat, thereby forming a stretched elastic film;

allowing the stretched elastic film to relax to achieve a relaxation percentage of about 10% or more; and laminating a nonwoven web facing to the relaxed elastic film, wherein the composite exhibits a heat shrinkage of about 40% or ore after being heated in water at 160° F. for 30 seconds to 1 minute.

2. The method of claim 1, wherein the propylene/α-olefin copolymer has a propylene content of from about 60 mole % to about 99.5 mole % and an α-olefin content of from about 0.5 mole % to about 40 mole %.

3. The method of claim 1, wherein the propylene/α-olefin copolymer has a density of from about 0.85 to about 0.88 grams per cubic centimeter.

4. The method of claim 1, wherein the α-olefin of the copolymer includes ethylene.

5. The method of claim 1, wherein the propylene/α-olefin copolymer is single-site catalyzed.

6. The method of claim 1, wherein the elastic film is stretched at a stretch ratio of from about 2.0 to about 4.5.

7. The method of claim 1, wherein the relaxation percentage is about 20% to about 50%.

8. The method of claim 1, further comprising winding the composite onto a roll, wherein the composite is substantially inhibited from retracting in the machine direction during winding onto the roll.

9. The method of claim 1, wherein the elastomer is selected from the group consisting of styrene-butadiene, styrene-isoprene, styrene-butadiene-styrene, styrene-isoprene-styrene, styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)styrene-(ethylene-propylene), and styrene-ethylene-(ethylene-propylene)-styrene, and combinations thereof.

10. The method of claim 1, wherein the elastomer constitutes about 60 wt. % or more of the polymer content of the elastomeric composition.

11. The method of claim 1, wherein the elastomeric composition contains about 10 wt. % or less of semi-crystalline polyolefins.

12. The method of claim 1, wherein the propylene/α-olefin copolymer constitutes about 20 wt. % or more of the polymer content of the thermoplastic composition.

13. The method of claim 1, wherein the film is a blown film.

14. The method of claim 1, wherein the nonwoven web facing contains a spunbond web, meltblown web, or a combination thereof.

15. The method of claim 1, further comprising laminating a second nonwoven web facing to the relaxed elastic film.

16. The method of claim 1, wherein the composite exhibits a heat shrinkage of about 50% or more after being heated in water at 160° F. for 30 seconds to 1 minute.

17. The method of claim 1, wherein the composite exhibits a heat shrinkage of about 60% or more after being heated in water at 160° F. for 30 seconds to 1 minute.

18. The method of claim 1, wherein the film is formed by being blown into nip rolls.

19. The method of claim 18, wherein the nip rolls are at a temperature sufficient to quench the film.

20. The method of claim 19, wherein the stretching comprises passing the quenched film through first and second sets of rolls, wherein the first set of rolls is traveling at a speed that is slower than the second set of rolls.

21. The method of claim 1, wherein the film is uniaxially stretched in the machine direction.

* * * * *

UNITED STATES PATENT AND TRADEMARK OFFICE
CERTIFICATE OF CORRECTION

PATENT NO. : 8,709,191 B2
APPLICATION NO. : 12/120984
DATED : April 29, 2014
INVENTOR(S) : Janis Wilson Hughes et al.

Page 1 of 1

It is certified that error appears in the above-identified patent and that said Letters Patent is hereby corrected as shown below:

In the Claims

Claim 1 (column 23, line 25)

"...about 40% or ore after being heated in water at 160° F..." should read --...about 40% or more after being heated in water at 160° F...--

Signed and Sealed this
Fifth Day of August, 2014

Michelle K. Lee
*Deputy Director of the United States Patent and Trademark Office*